United States Patent [19]
Ales

[11] Patent Number: 4,648,928
[45] Date of Patent: Mar. 10, 1987

[54] METHOD AND APPARATUS FOR APPLYING DISCRETE STRIPS OF MATERIAL TO A LONGITUDINALLY EXTENDING WEB

[75] Inventor: Thomas M. Ales, Winnebago County, Wis.

[73] Assignee: Kimberly-Clark Corporation, Neenah, Wis.

[21] Appl. No.: 833,688

[22] Filed: Feb. 27, 1986

[51] Int. Cl.⁴ .................. B32B 31/08; B32B 31/18; A61F 13/16
[52] U.S. Cl. .................................. 156/164; 156/177; 156/193; 156/250; 156/440; 156/510
[58] Field of Search ............... 156/164, 177, 191, 193, 156/250, 271, 439, 440, 510, 522, 544

[56] References Cited
U.S. PATENT DOCUMENTS

| | | | |
|---|---|---|---|
| 3,424,067 | 1/1969 | Blair | 156/440 |
| 3,607,563 | 9/1971 | Bagnall | 156/177 |
| 3,616,007 | 10/1971 | Anderson | 156/193 |
| 3,903,575 | 9/1975 | Plaskett | 156/191 |
| 4,578,133 | 3/1986 | Oshefsky et al. | 156/164 |

Primary Examiner—Michael Ball
Assistant Examiner—Geoffrey L. Knable
Attorney, Agent, or Firm—Douglas L. Miller; Donald L. Traut; Jeremiah J. Duggan

[57] ABSTRACT

A method and apparatus for applying discrete strips of material to both longitudinally opposite segments of a longitudinally extending web, comprising: longitudinally moving the web along a travel path including a helically looped portion having a center axis and passing opposite longitudinal edges of the web in lapping proximity to one another in a lapping zone of the looped portion; applying at least one continuous strip of material to the web by transversely oscillating the strip across the opposite longitudinal edges in the lapping zone of the travel path; and severing the applied strip between the edges in the lapping zone. The method and apparatus of the present invention have utility in forming elastic gathers on fibrous web materials, such as may subsequently be processed for end-use applications such as disposable diapers, panty-type garments and the like.

20 Claims, 3 Drawing Figures

METHOD AND APPARATUS FOR APPLYING DISCRETE STRIPS OF MATERIAL TO A LONGITUDINALLY EXTENDING WEB

BACKGROUND OF THE INVENTION

1. Field Of The Invention

This invention relates generally to method and apparatus for applying discrete strips of material to a longitudinally extending web and has utility in applying strips of elastic material to a longitudinally moving web of material as is carried out, for example, in the manufacture of disposable diapers, panty garments and the like.

2. Description Of Related Art

The use of a stationary mandrel around which a longitudinally travelling web is helically wound is disclosed in the art, for example, U.S. Pat. No. 2,696,244 to P. T. Jackson, Jr., and in U.S. Pat. No. 2,841,202 to H. W. Hirschy. In the systems disclosed in these patents, a second web or a plurality of threads is superimposed over a travelling base web which is helically wound about the mandrel. A rotating creel or carrier is orbited about the longitudinal axis of the mandrel and carries dispensing means to feed the second web or plurality of threads over the travelling base web. Each of these patents further discloses the use of a slitter knife to cut the overlaid web or threads.

U.S Pat. No. 4,479,836 to W. E. Dickover, et al discloses a method for continuous or intermittent securing of a moving elastic member or band to a moving web of disposable diaper components along a longitudinal axis or seam of a travelling web, as illustrated, for example, in FIG. 15 thereof. The elastic strips in the system disclosed in this patent are applied over a single wide sheet which subsequently is cut into discrete web articles, or alternatively, the elastic strips are applied over a plurality of side-by-side aligned webs travelling in a parallel direction (column 12, line 15 et seq.).

SUMMARY OF THE INVENTION

In one aspect, the present invention relates to a method of applying discrete strips of material to both longitudinally opposite segments of a longitudinally extending web, comprising: longitudinally moving the web along a travel path including a helically looped portion having a center axis and passing opposite longitudinal edges of the web in lapping proximity to one another in a lapping zone of the looped portion; applying at least one continuous strip of material to the web by transversely oscillating the strip across the opposite longitudinal edges in the lapping zone of the travel path; and severing the applied strip between the edges in the lapping zone.

Another aspect of the invention relates to a method as described above, wherein the web is gatherable and the continuous strip of material comprises an elastic material.

Another aspect of the invention relates to a method of the foregoing type, wherein the discrete strips of material are applied to the web as arcuate strips by applying the continuous strip to the web by tranversely oscillating the strip along a straight line, e.g., a straight line parallel to the center axis of the helically looped portion of the travel path, passing transversely across the edges in the lapping zone.

A further aspect of the invention relates to a method of the foregoing type, wherein the helically looped portion of the travel path defines an arc length of greater than 360°.

Yet another aspect of the invention relates to a method of the aforementioned type, wherein the discrete strips are disposed on each longitudinally opposite segment of the web in semi-circular arcs, the projection onto a plane perpendicular to the center axis of the helically looped portion of the travel path is circular, and the moving web has a longitudinal centerline defining an approach angle and an exit angle as defined below which are equal to each other and wherein:

$$D = \frac{\sqrt{(nl)^2 - w^2}}{\pi} \text{ and } \gamma = \arcsin(w/l)$$

wherein: D = diameter, in inches, of the circular projection of the helically looped portion of the travel path; l = longitudinal distance, in inches, measured along the web edge between corresponding repeating semi-circular arcs of the strip; n = an integer having a value of at least 1; w = width, in inches, of the web; and γ = each of the web approach and exit angles separately as measured, respectively, between a coplanar projection of a line perpendicular to the center axis of the helically looped portion of the travel path and the longitudinal centerline of the segments of the web approaching and leaving the helically looped portion of the travel path.

In another aspect, the present invention relates to an apparatus for applying discrete strips of material to both longitudinally opposite segments of a longitudinally extending web, comprising: web transport means for longitudinally moving the web along a travel path including a helically looped portion having a center axis to pass opposite longitudinal edges of the web in lapping proximity to one another in a lapping zone of the looped portion; strip applicator means for applying at least one continuous strip of material to the web by transversely oscillating the strip across the opposite longitudinal edges in the lapping zone of the travel path; and severing means for severing the applied continuous strip between the edges in the lapping zone.

A further aspect of the invention relates to an apparatus of the aforementioned type, wherein the web transport means comprises: (a) a stationary cylindrical mandrel around which the web is helically looped so that the center axis of the looped portion is coincident with the longitudinal axis of the mandrel; (b) web feed means dimensioned and configured to introduce the web onto the mandrel at a selected approach angle between the longitudinal centerline of a segment of the web approaching the mandrel and a line perpendicular to the longitudinal axis of the mandrel; and (c) web take-off means dimensioned and configured to remove the web longitudinal from the mandrel at a selected exit angle between the centerline of the web and a line perpendicular to the longitudinal axis of the mandrel.

A still further aspect of the invention relates to an apparatus of the aforementioned type, wherein the web transport means is dimensioned and configured so that the following relationships are satisfied:

$$D = \frac{\sqrt{(nl)^2 - w^2}}{\pi} \text{ and } \gamma = \arcsin(w/l)$$

wherein: D = diameter, in inches, of the mandrel; l = longitudinal distance, in inches, measured along the web edge between corresponding repeating arcuate segments of the applied strip; n=an integer having a value of at least 1; w=width, in inches, of the web; and γ=web approach and exit angles separately as measured, respectively, between a coplanar projection of a line perpendicular to the axis of the mandrel and a longitudinal centerline of the segments of the web approaching and leaving the mandrel.

DETAILED DESCRIPTION OF THE PREFERRED EMBODIMENTS

Figure 1:
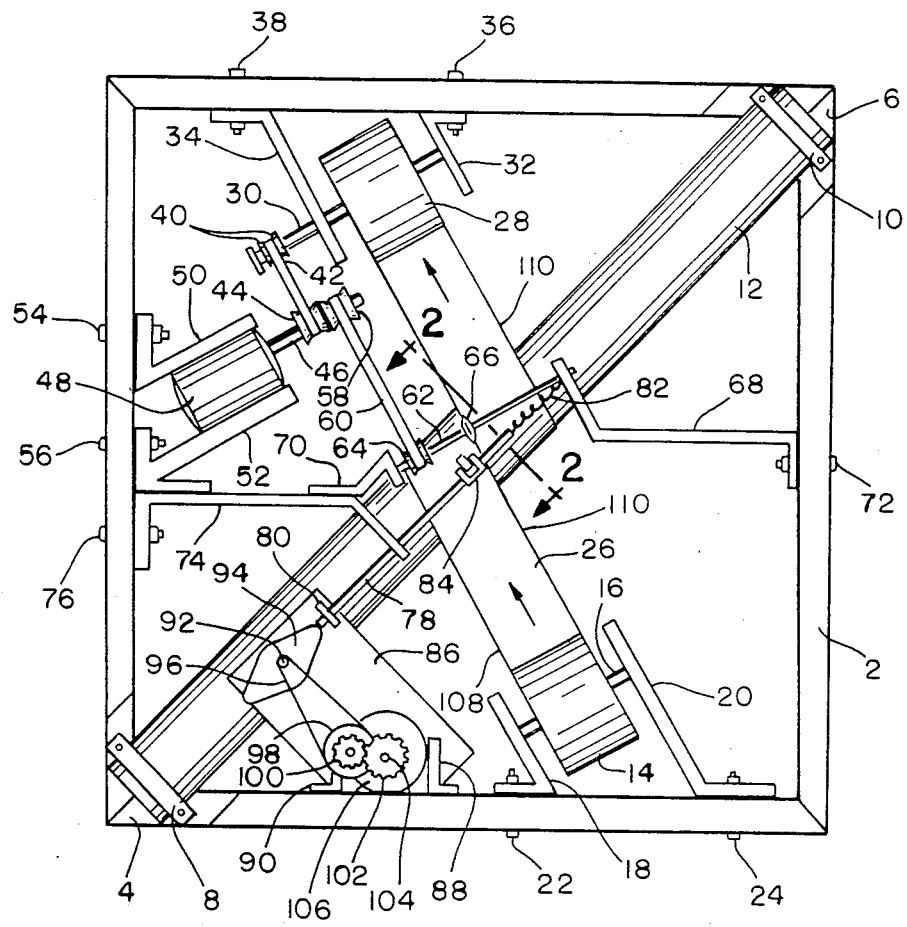
FIG. 1 is a schematic plan view of apparatus for applying discrete strips of material to a longitudinally moving web in accordance with one embodiment of the present invention.

The longitudinally extending web utilized in the present invention may be formed of any suitable material which is capable of being longitudinally moved along a travel path including a helically looped portion to pass opposite longitudinal edges of the web in lapping proximity to one another, and to which the discrete strips of material may be applied. In a particularly useful embodiment, the web is a gatherable web of material, meaning that when an elastic strip under tension is applied to the web, upon release of the forces tensioning the elastic strip, the strip will contract to form puckers or gathers in the web, thereby providing an elasticized portion of the web along the segment on which the elastic strip is attached. The web may be fibrous or non-fibrous in character, with fibrous webs being woven or nonwoven in character and may be formed of any suitable natural and/or synthetic materials. In the case of fibrous webs, such materials may include textile fibers such as cotton, rayon, linen, etc., and/or synthetic fibers such as polyolefins, acrylics, polyesters, etc. The web may also be in the form of a plastic or elastomeric film or sheet, formed of any suitable material, such as polyethylene, polyurethane, acrylic polymers and copolymers, etc. Further, the web may be a single layer or may comprise a composite of two or more layers of material. For applications such as the manufacture of disposable diapers and panty-type garments, composite webs are generally useful, comprising a fibrous layer and a synthetic organic polymeric ("plastic") film layer, wherein the fibrous layer may be made of nonwoven material such as spunbonded olefinic fibers or bonded carded olefinic fibers, e.g., spunbonded polypropylene fibers. The plastic film in such composites may be formed of materials such as polyethylene, polypropylene, polyurethane, and acrylic polymers and suitable copolymers. A preferred composite material for the aforementioned panty-type garment applications is ethylene methacrylate (EMA) coated onto a polypropylene fiber nonwoven material.

Likewise, the material of which the discrete strips are formed may be any suitable material which is capable of being applied to the longitudinally extending web in the manner of the present invention. The strip material may be, but need not be, elastic in character. However, the ability to apply elastic strips under tension to a web of gatherable material is advantageous in the practice of the present invention, for example in the manufacture of disposable diapers or panty-type garments, to form elastic gathers therefor. As an alternative to the use of discrete strip materials which are elastic in character, it may in some instances be advantageous to utilize discrete strip materials which are heat-shrinkable, so that subsequent to application of the strips to the web, heat shrinking of the strip elements will produce a gathering of the web to which such strips are applied.

As described hereinafter, the provision of arcuate, e.g., semi-circular strips is particularly advantageous in the manufacture of the aforementioned disposable diaper or other panty-type garments.

Among suitable elastic materials for the discrete strips applied to the web in the practice of the present invention, are butadiene/acrylonitrile copolymers, styrene/isoprene copolymers, polyurethane elastomers, and the like. Useful elastic materials include hot-melt extrudable materials, especially those which are self-adhering in character. Preferred hot-melt extrudable, self-adhering materials include thermoplastic synthetic resin and rubber block copolymer compositions, such as those described in U.S. Pat. No. 4,418,123 to Bunnelle and commercially available from H. B. Fuller Company as FULLASTIC® extruded self-adhering elastics; TUFTANE® elastic adhesive commercially available from B.F. Goodrich Company, which is a polyurethane based composition; and Borden 6341 hot-melt adhesive, available from The Borden Company. As used herein, the term "applying" or "application" in reference to providing the discrete strips on the web includes the step(s) or bonding, if required, of the strips to the substrate, such as by coating of the strips with a bonding medium, e.g., an adhesive, prior to or subsequent to physical placement of the discrete strips on the web. As indicated above, preferred elastic materials for the practice of the present invention, include self-adhering elastic materials which upon physical placement on the web, optionally with pressure contacting of the strip applied to the web, such as by passage thereof through a pressure nip roll assembly, are suitable to retain the strip in position on the web. Alternatively, the strip material may be coated prior to its placement on the web with a heat-activatable bonding medium, with the web and applied strip thereafter being heated to sufficient temperature to activate the bonding medium and adhesively bond the strip to the web.

As used herein, the term "elastic" as used to characterize the discrete strips of material which are applicable to the longitudinally extending web in the practice of the present invention refers to materials which, either as applied or upon heat-shrink treatment after application, can be stretched to an elongation greater than the untensioned dimension thereof and which, upon release of the tensioning force, can recover a substantial portion of the elongation. For example, suitable elastic materials useful as discrete strip materials in the present invention are those which can be stretched to an elongation of at least about 25% of their relaxed dimensions, i.e., which can be stretched to at least about one and one-fourth times their relaxed dimensions, and upon release of the stretching force will recover at least about 40% of the elongation, i.e., in the case of being elongated to 125% of its untensioned dimension, will contract to not more than about 115% of its relaxed length. At least for some purposes of the present invention, elastic materials which upon release of the stretching force recover all or nearly all of their elongation are preferred and many elastic materials are available which can be elongated to considerably more than 125% of their relaxed dimension.

As used herein, the term "longitudinally extending" used in reference to the web means that the web processed in accordance with the present invention has a length dimension substantially greater than its width dimension; in such context, the term "transversely" refers to a direction which is generally perpendicular to the longitudinal direction of the web, e.g., as defined by a longitudinal centerline of the web. Continuous webs of material fed to the process from a large roll thereof are usually utilized.

Referring now to the drawings, FIG. 1 is a plan view of apparatus for applying discrete strips, such as arcuate strips, of material to a longitudinally extending web in accordance with one embodiment of the present invention. The apparatus comprises a frame member 2, which in plan view is of generally rectangular or square form. Extending diagonally across the frame and reposed in recesses 4 and 6 where it is secured respectively by retainer brackets 8 and 10, respectively, is mandrel 12. The mandrel may be of any suitable material of construction, such as steel or aluminum, and preferably has a surface characterized by a low coefficient of friction, such as may be provided by polishing of the mandrel surface to a mirror finish, or alternatively by coating of the mandrel surface with a low coefficient of friction coating, e.g., a Teflon ® polymer coating. The mandrel is of cylindrical shape having, in the illustrated embodiment, a circular cross section. (The term "cylindrical" as used herein has its usual meaning of including cylindrical members of non-circular, e.g., oval cross section.)

A web feed roll 14 is mounted on spindle 16, the spindle 16 in turn being supported by bracket members 18 and 20, which are respectively secured to the frame member 2 by means of nut/bolt fastener assemblies 22 and 24, respectively. At the other longitudinally opposite end of the web 26 is web take-up roll 28 mounted on spindle 30, the spindle in turn being mounted for rotation in bracket members 32 and 34, secured to the frame member 2 by fastener assemblies 36 and 38, respectively.

Spindle 30 has flange protrusions 40 at one end accommodating a drive belt 42 coupled at its opposite end to pulley fixture 44 mounted on drive shaft 46. The drive shaft is coupled to drive motor 48 mounted in position by bracket members 50 and 52, with the bracket members being joined to the frame member 2 by fastener assemblies 54 and 56, respectively.

Disposed on drive shaft 46 is a second pulley fixture 58 coupling drive belt 60 to shaft 62. Shaft 62 has flange protrusions 64 thereon to retain drive belt 60 in position during operation. Also mounted on shaft 62 is severing means 66, described more fully hereinafter. Opposite ends of shaft 62 are mounted for rotation in bracket members 68 and 70, respectively, bracket member 68 being secured to frame member 2 by fastener assembly 72 and bracket member 70 being joined, such as by welding, to bracket member 74, which is mounted on frame member 2 by fastener assembly 76.

The bracket member 74, in addition to functioning as a support element for bracket member 70, comprises an outer end in which a push rod 78 is reposed. Push rod 78 likewise extends through end bracket 80 and is joined to bias spring 82 which is permanently affixed to bracket member 68. Between the bracket members 68 and 74, a strip applicator assembly 84 is mounted.

End bracket 80 is mounted on a support plate 86 attached, as by welding, to the bracket members 88, 90 in turn joined, as by welding, to frame member 2. Disposed on support plate 86 is a shaft 92 on which is mounted cam 94, the shaft being coupled by drive belt 96 to pulley fixture 98. The pulley fixture has on its top surface a driven gear wheel 100 in contact with a driver gear wheel 102. The driver gear wheel is mounted on drive shaft 104 of drive motor 106 mounted by means of bracket members 88 and 90 to frame member 2.

In operation, the web 26, which has opposite longitudinal edges as supplied by feed roll 14, is longitudinally moved in the direction indicated by the arrow along a travel path including a helically looped portion, defined by the passage of the web over stationary mandrel 12, to pass opposite longitudinal edges of the web in lapping proximity to one another in a lapping zone of the looped portion. Thus, the opposite longitudinal edges 108 and 110 are associated with separate turns of the web on the mandrel and as a result the edges are lapped in the helical loop and lie in proximity, preferably abutting one another.

Concurrently, the drive motor 48 by means of belt 42 effects rotation of spindle 30 to cause take-up of the web discharged from the mandrel, in take-up roll 28.

As used herein, the term "web transport means" in reference to the aforementioned apparatus elements is inclusive of: (a) the stationary cylindrical mandrel 12 around which the web is helically looped so that the center axis of the looped portion is coincident with the longitudinal axis of the mandrel; (b) the web feed means including spindle 16, on which the feed roll 14 is mounted, and bracket members 18 and 20, together with fastener assemblies 22 and 24, such web feed means serving to introduce the web onto the mandrel at a selected approach angle between the longitudinal centerline of a segment of the web approaching the mandrel and a line perpendicular to the longitudinal axis of the mandrel; and (c) web take-off means including spindle 30, bracket members 32 and 34 and their fastener assemblies 36 and 38, as well as drive belt 42 and the coupling means associated therewith for drive motor 48, such take-off means serving to remove the web from the mandrel at a selected exit angle between the longitudinal centerline of the web and a line perpendicular to the longitudinal axis of the mandrel.

Although the web subsequent to application of the discrete strips of material thereto is shown as being taken up in a roll 28, it will be apparent that in various applications of the present invention, it may be advantageous to instead transport the web to further processing steps, such as severing of the web into discrete product articles or otherwise further processing the web for its desired end use. Accordingly, the aforementioned term "web transport means" in respect of the web take-off means is intended to include such alternative means for removing the web from the helically looped portion of its travel path subsequent to application of the discrete strips and severing of the web, as described hereinafter in greater detail.

As the edges of the web in the helically looped portion of the travel path lie in lapping proximity in the lapping zone of the helically looped portion of the web defined by the mandrel 12, the strip material is applied to the web 26 by means of strip applicator assembly 84, as described hereinafter in greater detail. The strip applicator assembly 84 is transversely oscillated so that the applied strip is correspondingly transversely oscillated across the edges of the web segments in the lapping zone. Such transverse oscillation, which in the embodiment shown is in a straight line which is parallel to the center axis of the helically looped zone, i.e., parallel to the longitudinal axis of mandrel 12, is effectuated by rotation of cam 94 via drive motor 106 so that the attached driver gear wheel rotates pulley fixture 98 and drive belt 96, and the cam is rotated to impart reciprocating movement to the push rod 78 whose end is in contact with the cam peripheral surface. The push rod, being reposed in end bracket 80 and bracket member 74, is retained in position for straight line oscillating movement, as mediated by bias spring 82, which serves to retain the push rod opposite end in continuous contact with the peripheral surface of the cam 94.

Concurrently, the rotation of drive shaft 46 by drive motor 48 effects rotation of pulley fixture 58 causing the drive belt 60 to rotate shaft 62 having severing means 66 positioned thereon. The severing means may suitably comprise a rotary knife element or other bladed or serrated cutting means which function to sever the strip applied by the strip applicator assembly 84 between the edges 108, 110 of the web in the lapping zone of the helically looped portion of the web's travel path. The strip applicator assembly is continually supplied with strip material from a source which is not shown for the sake of simplicity of illustration.

In such manner, it is seen that the strip applicator assembly will apply strip material to the web in a serpentine pattern as a result of the transverse straight line oscillation of the assembly across the web longitudinal edges 108, 110 in the lapping zone, and that with continuous movement of the web along the travel path in the direction indicated by the arrows in the drawing, the lapped edges having the strip material applied thereacross will come into contact with the severing means 66 which serves to sever the applied strip between such web edges. In such manner arcuate strips are formed in both longitudinally opposite segments of the longitudinally extending web, i.e., the segments of the web which respectively are being introduced to and discharged from the helically looped portion of the travel path.

Figure 2:
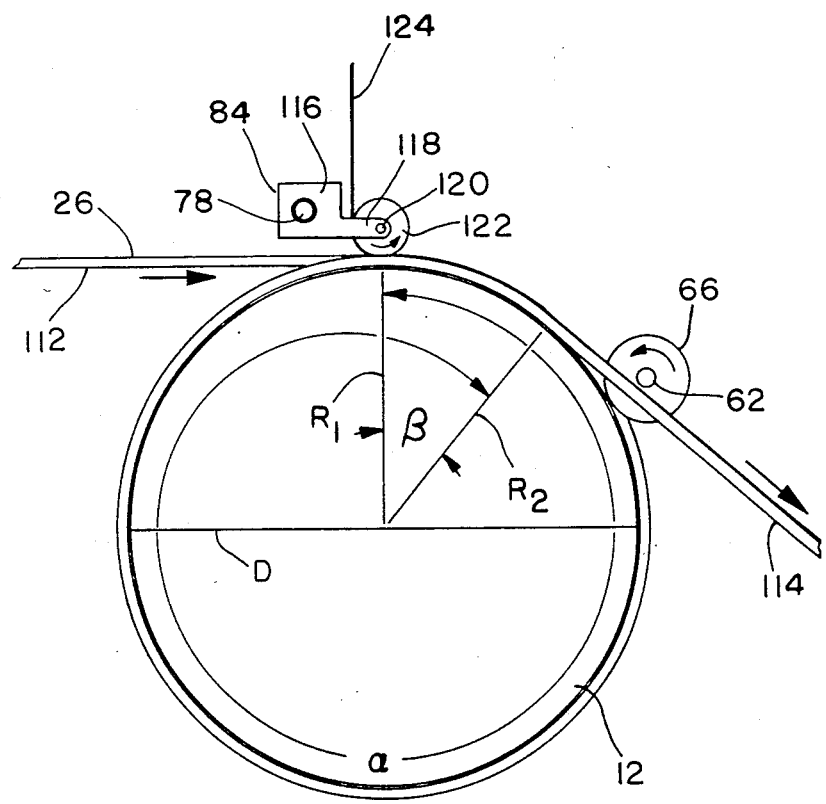
FIG. 2 is a simplified partial section view on an enlarged scale, taken along line 2—2 of FIG. 1.

FIG. 2 illustrates the details of the helically looped portion of the travel path, including the lapping zone thereof. (Cross section hatch lines which would conventionally be employed on the cross section of mandrel 12 are omitted in FIG. 2 for clarity of illustration).

The mandrel 12, of diameter D, is engaged by the web 26 with (FIG. 3) a longitudinally extending segment 112 of the web approaching mandrel 12 and a longitudinaly extending segment 114 leaving mandrel 12. Web 26 is helically wound about the outer cylindrical surface of mandrel 12 in a helical loop, so that corresponding portions of edges of the web 26 are in lapping proximity to one another, as previously described. The helically looped portion of the web's travel path thus is measured by an arc length shown as angle alpha in the drawing, so that the arc length of the helically looped portion is greater than 360°, as is desirable to provide a lapping zone affording sufficient lengths of lapped edges to effect application of the strip material and subsequent severing of same. $R_1$ is perpendicular to the approaching web 112 and $R_2$ is perpendicular to the exiting web 114. Accordingly, it is seen that an angle beta between radii $R_1$ and $R_2$ is formed such that the corresponding edges of the respective turns of the webs are in lapping proximity to one another.

The strip applicator assembly 84 is mounted on shaft 78 for axially reciprocating movement in the manner previously described. The body 116 of the strip applicator assembly terminates in a forwardly extending fork 118 on which is mounted an axle 120 in turn having a pressure wheel 122 mounted thereon. The strip applicator assembly receives strip material 124 from a source of same (not shown) and the strip is applied to the web by transverse oscillation of the strip applicator assembly in the previously described manner. Pressure wheel 122 serves to press the strip material against the web segments 112, 114 to ensure efficient contacting and application of the strip to the web. As indicated, the strip material may be self-adhesive in character, whereby the strip material by the simple expedient of compression against the web by means of pressure wheel 122 is secured to the web. Alternatively, it may be suitable in some applications of the present invention to utilize strip material which is coated with an adhesive or other bonding medium, e.g., a coating of heat-activatable adhesive, such that the pressure wheel may be internally heated (by means not shown) to raise the temperature of the applied strip to sufficient level to activate the bonding medium and secure the strip of material to the web. In other applications of the invention, the strip may be applied and bonded to the web subsequent to its application, but prior to its severing. As previously mentioned, the terms "applying" and "application" in reference to the discrete strips of material are intended to be broadly construed to include all such methods by which the strips are secured to the web, including, in addition to the aforementioned application of external bonding media, ultrasonic or laser welding of strip materials to webs, extrusion casting of a securing overlay film to the web having the discrete strips positioned thereon, etc.

In any event, subsequent to application of the strip material 124 to the web, the lapped segments are translated over the surface of the mandrel to be severed by the severing means mounted on shaft 62. As indicated hereinabove, the severing means may suitably comprise a cutting wheel having a blade surface at its periphery, such element being fixedly positioned as best shown in FIG. 1 to sever the applied strip between the web edges in the lapping zone. Once severed, the segment 114 at the discharge end, having arcuate strips of material formed thereon is discharged from the lapping zone for take-up and end-use application or further processing steps.

As indicated the strip material may be elastic in character, and in some applications of the present invention it may be desirable to apply the strip under tension to the web, whereby the web is incrementally gathered by the strip upon release of the tension. Such tensioned application of the strip to the web to serve as elastic gathers is highly advantageous in the manufacture of disposable panty-type garments and other articles of similar type, wherein the elastic element provides for conformability of fit of the garment to the wearer.

Figure 3:
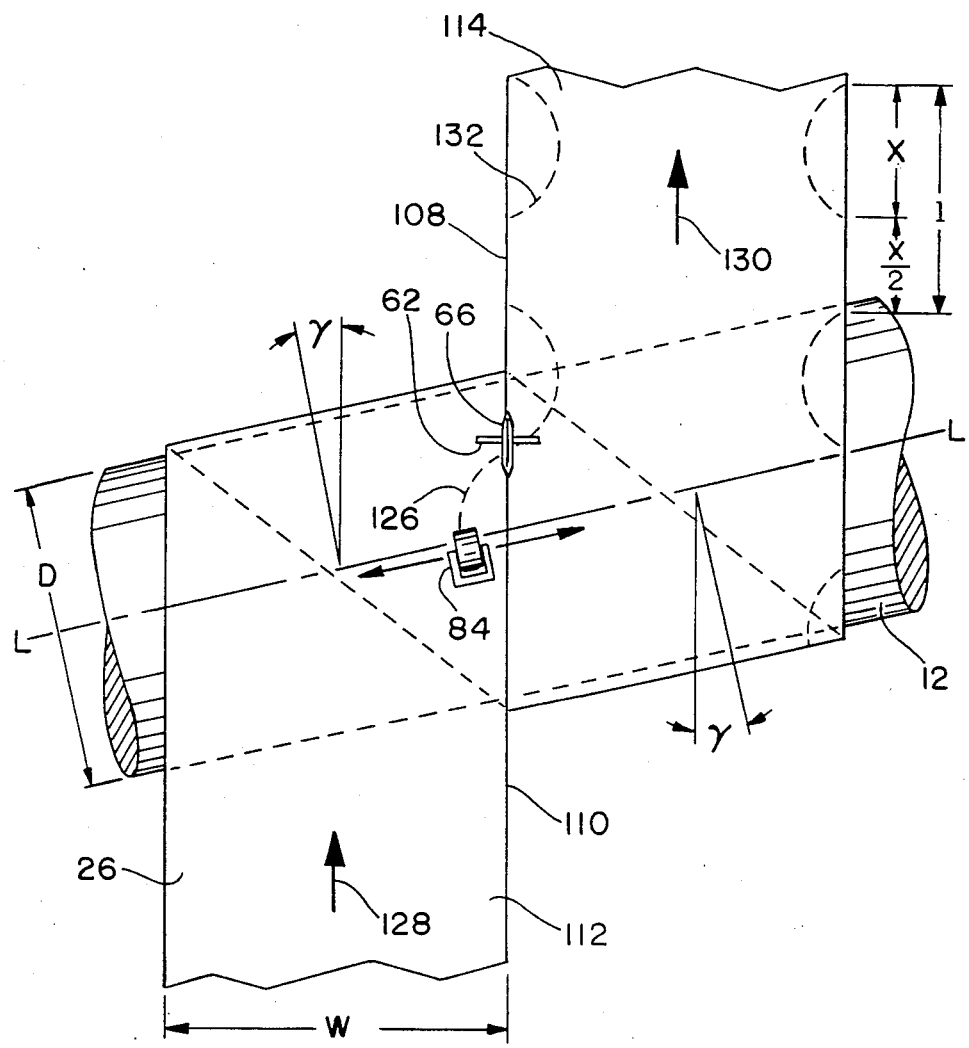
FIG. 3 is a simplified plan view on an enlarged scale of a portion of the apparatus of FIG. 1 in the vicinity of line 2—2.

FIG. 3 is a simplified plan view of a portion of the system shown in FIGS. 1 and 2, wherein the same reference numerals are used to identify the same system elements, and wherein the various geometric and dimensional characteristics of the system are shown. The mandrel 12 has a longitudinal centerline L—L and a diameter D. Longitudinally opposite segments 112, 114 of the web 26 are shown as being helically looped by passage over the mandrel. The web has a width W and is passed over the mandrel in such manner as to place the longitudinal edges 110, 108 of the respective segments in abutting relationship, as shown. The strip applicator assembly 84 traverses the marginal portions of the lapped, abutting web segments in the serpentine path indicated by dotted line 126 to apply the strip of material to the web in such pattern. With continued translation of the web along the travel path, in the direction indicated by arrows 128 and 130 the lapped portion of the respective web segments is brought into position for severing of the applied strip between edges 108, 110 in the previously described manner. As a result, there is formed a series of arcuate strips 132 of material on longitudinally opposite segments of the longitudinally extending web.

In preferred practice, the arcuate strips 132 are semi-circular in form, with equal and opposite patterns being applied to the respective web segments in the lapping zone, such that the applied strip pattern will repeat with a longitudinal distance on the web for the arcuate strip (shown as dimension X in FIG. 3) being twice the longitudinal distance (shown as X/2) between the ends of adjacent semi-circular strips. In such preferred embodiment, wherein the projection onto a plane perpendicular to the center axis of the helically looped portion of the travel path is circular, and the approach and exit angles (each of which is equal to the other and which are shown as angle gamma in FIG. 3) is measured by a coplanar projection of a line perpendicular to the longitudinal axis L—L of the helically looped portion of the travel path, i.e., a line perpendicular to the longitudinal axis of the mandrel 12, and the longitudinal centerline of the web, the relationships between the diameter, D, of the circular cross-section of the helically looped portion of the travel path, i.e., the diameter of the mandrel, and the approach and exit angles are governed by the relationships:

$$D = \frac{\sqrt{(nl)^2 - w^2}}{\pi} \text{ and } \gamma = \arcsin(w/l)$$

wherein: D=diameter, in inches, of the circular projection of the helically looped portion of the travel path; l=longitudinal distance, in inches, measured along the web edge between corresponding repeating semi-circular arcs of the strip; n=an integer having a value of at least 1; w=width, in inches, of the web; and $\gamma$=each of the web approach and exit angles separately as measured, respectively, between a coplanar projection of a line perpendicular to the center axis of the helically looped portion of the travel path and the longitudinal centerline of the web segments approaching and leaving the helically looped portion of the travel path, respectively.

Although the invention has been illustratively described with reference to a helically looped portion of the travel path for the longitudinally extending web wherein the web segments define two "turns" on the mandrel or other support means, it will be apparent that other applications of the invention may utilize a greater number of "turns" of the web in the lapping zone, such that strip materials can be applied to more than two web segments concurrently. Further, although the web preferably is a continuous material as shown, it may be desirable in some applications of the present invention to utilize a foraminous web or other web structure which has openings, perforations or cut-outs therein, as useful in the desired end-use application of the web.

What is claimed is:
1. A method of applying discrete strips of material to both longitudinally opposite segments of a longitudinally extending web, comprising:
longitudinally moving the web along a travel path including a helically looped portion having a center axis and passing opposite longitudinal edges of the web in lapping proximity to one another in a lapping zone of said looped portion;
applying at least one continuous strip of material to the web by transversely oscillating the strip across the opposite longitudinal edges in the lapping zone of the travel path; and
severing the applied strip between said edges in the lapping zone.

2. A method according to claim 1, wherein the web is a gatherable web and the continuous strip of material comprises an elastic material.

3. A method according to claim 1 or claim 2, wherein the discrete strips of material are applied to the web as arcuate strips by applying the continuous strip to the web by transversely oscillating the strip along a straight line passing transversely across said edges in the lapping zone.

4. A method according to claim 3, including transversely oscillating the strip along a straight line parallel to the center axis of the helically looped portion of the travel path.

5. A method according to claim 2, wherein the web is a composite web comprising a fibrous layer and a synthetic organic polymeric film layer.

6. A method according to claim 5, wherein the fibrous layer comprises a nonwoven material.

7. A method according to claim 2, including applying the continuous strip of material to the web under tension.

8. A method according to claim 7, wherein the strip comprises a self-adhering elastic material.

9. A method according to claim 1 or claim 2, wherein the helically looped portion of the travel path defines an arc length greater than 360°.

10. A method according to claim 1 or claim 2, including passing the web over a stationary mandrel of cylindrical configuration to define the helically looped portion of the travel path.

11. A method according to claim 1, wherein the web comprises a gatherable web and the continuous strip of material comprises an elastic strip which is applied under tension to the web, whereby the web is gathered by contraction of the strip upon release of said tension.

12. A method according to claim 11, wherein the discrete strips of material are applied to the web as arcuate strips by applying the continuous strip to the web by transversely oscillating the strip along a straight line passing transversely across said edges in the lapping zone.

13. A method according to claim 1 or claim 2, wherein the opposite longitudinal edges of the web in the helically looped portion of the travel path abut one another.

14. A method according to claim 1 or claim 2, wherein said web is a continuous web and including continuously moving the web along said travel path.

15. A method according to claim 3, wherein the discrete strips are disposed on each longitudinally opposite segment of the web in semi-circular arcs, the projection onto a plane perpendicular to the center axis of the helically looped portion of the travel path is circular, and the moving web has a longitudinal centerline defining an approach angle and an exit angle as defined below which are equal to each other and wherein:

$$D = \frac{\sqrt{(nl)^2 - w^2}}{\pi} \text{ and } \gamma = \arcsin(w/l)$$

wherein:
- D = diameter, in inches, of the circular projection of the helically looped portion of the travel path;
- l = longitudinal distance, in inches, measured along the web edge between corresponding repeating semi-circular arcs of the strip;
- n = an integer having a value of at least 1;
- w = width, in inches, of the web;
- γ = each of web approach and exit angles separately as measured, respectively, between a coplanar projection of a line perpendicular to the center axis of the helically looped portion of the travel path and the longitudinal centerline of the segments of the web approaching and leaving the helically looped portion of the travel path.

16. Apparatus for forming discrete strips of material on both longitudinally opposite segments of a longitudinally extending web, comprising:
    web transport means for longitudinally moving the web along a travel path including a helically looped portion having a center axis to pass opposite longitudinal edges of the web in lapping proximity to one another in a lapping zone of the looped portion;
    strip applicator means for applying at least one continuous strip of material to the web by transversely oscillating the strip across said opposite longitudinal edges in the lapping zone of the travel path; and
    severing means for severing the applied continuous strip between said edges in the lapping zone.

17. Apparatus according to claim 16 wherein the strip applicator means is dimensioned and configured to apply the continuous strip of material to the moving web by oscillating the strip in a straight line to provide the discrete strips as arcuate strips.

18. Apparatus according to claim 16 or claim 17, wherein the web transport mean comprises: (a) a stationary cylindical mandrel around which the web is helically looped so that the center axis of the looped portion is coincident with the longitudinal axis of the mandrel; (b) web feed means dimensioned and configured to introduce the web onto the mandrel at a selected approach angle between the longitudinal centerline of a segment of the web approaching the mandrel and a line perpendicular to the longitudinal axis of the mandrel; and (c) web take-off means dimensioned and configured to remove the web from the mandrel at a selected exit angle between the longitudinal centerline of a segment of the web and a line perpendicular to the longitudinal axis of the mandrel.

19. Apparatus according to claim 18, wherein the mandrel has a circular cross-section.

20. Apparatus according to claim 19, wherein the web transport means is dimensioned and configured so that the following relationships are satisfied:

$$D = \frac{\sqrt{(nl)^2 - w^2}}{\pi} \text{ and } \gamma = \arcsin(w/l)$$

wherein:
- D = diameter, in inches, of the mandrel;
- l = longitudinal distance, in inches, measured along the web edge between corresponding repeating arcuate segments of the applied strip;
- n = an integer having a value of at least 1;
- w = width, in inches, of the web; and
- γ = each of web approach and exit angles separately as measured, respectively, between a coplanar projection of a line perpendicular to the mandrel's center axis and the longitudinal centerline of segments of the web approaching and leaving the mandrel.

* * * * *